United States Patent

Beddell et al.

[11] 3,992,365
[45] Nov. 16, 1976

[54] AGONIST ANALOGUES OF LUTEINIZING HORMONE RELEASING HORMONE

[75] Inventors: Christopher Raymond Beddell, Ashford; Lawrence Alfred Lowe, Swanley; Samuel Wilkinson, Beckenham, all of England

[73] Assignee: Burroughs Wellcome Co., Research Triangle Park, N.C.

[22] Filed: Oct. 31, 1974

[21] Appl. No.: 519,667

[30] Foreign Application Priority Data
Nov. 1, 1973 United Kingdom............... 50811/73
Oct. 10, 1974 United Kingdom............... 43917/74

[52] U.S. Cl. ....................... 260/112.5 LH; 424/177
[51] Int. Cl.² ................. C07C 103/52; A61K 37/00
[58] Field of Search........................... 260/112.5 LH

[56] References Cited
UNITED STATES PATENTS
3,853,834  12/1974  Shields ..................... 260/112.5 LH
3,880,825  4/1975  Sakakibara et al. ........ 260/112.5 LH Primary Examiner—Lewis Gotts
Assistant Examiner—Reginald J. Suyat
Attorney, Agent, or Firm—Donald Brown

[57] ABSTRACT

Novel peptide compounds of the formula

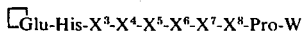

are provided together with their acid addition salts and their complexes with pharmaceutically acceptable metals. The compounds are LH-RH analogues and together with their salts and complexes exhibit LH-RH agonist activity. In the formula $X^3$ and $X^5$ are the same or different and each is phenylalanyl optionally substituted in the benzene ring;

$X^4$ and $X^6$ are the same or different and each is selected from glycyl, alanyl (D- or L-) and asparaginyl;

$X^7$ is a radical of a neutral hydrophobic nonsulphur containing non-heterocyclic amino acid;

$X^8$ is a radical of a basic amino acid or is glycyl or phenylalanyl optionally substituted in the benzene ring; and W is selected from glycine amide and a group $-NR^1R^2$.

All references are to the L-amino acids and their radicals except in the case of glycine and unless otherwise stated.

Also provided are methods for the preparation of the peptides, salts and complexes, pharmaceutical formulations containing them and methods for the preparation of such formulations, and methods for the use of the peptides, salts and complexes in human and in veterinary medicine.

27 Claims, No Drawings

AGONIST ANALOGUES OF LUTEINIZING HORMONE RELEASING HORMONE

This invention relates to peptides, their acid addition salts and complexes of the peptides with pharmaceutically acceptable metals; to the preparation of such peptides, salts and complexes; to formulations containing such peptides, salts or complexes and the preparation of such formulations; and to the use of the peptides, salts and complexes in human and veterinary medicine.

More particularly the present invention relates to analogues of luteinizing hormone — releasing hormone (LH-RH), a decapeptide having the structure

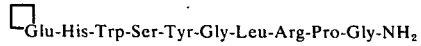
└─Glu-His-Trp-Ser-Tyr-Gly-Leu-Arg-Pro-Gly-NH$_2$

The abbreviations used herein for amino acids and their radicals are those conventional in the art and may be found in, for example, Biochemistry, 11, 1726 (1972). In the above and throughout the following all references are to the L-amino acids and their radicals except in the case of glycine and unless otherwise stated.

LH-RH is released from the mammalian hypothalamus into the veins of the hypothalamo-hypophyseal portal system and acts on the anterior pituitary to cause the release of two gonadotrophins, luteinizing hormone (LH) and follicle-stimulating hormone (FSH). LH stimulates the synthesis of steroid hormones in the gonads of both sexes and, in the female, also induces the ovulation of suitably matured ovarian follicles. FSH stimulates (in the female) the growth and maturation of ovarian follicles and (in the male) the growth of the seminiferous tubules and the early stages of spermatogenesis. The maturation of spermatozoa in the male is controlled by androgens whose formation is controlled by LH.

It has now been appreciated by the Applicants that if the sequence of LH-RH is written in the form:

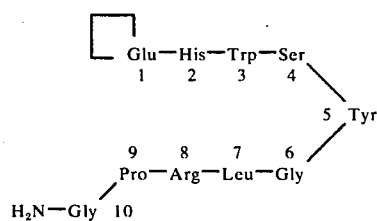

it is seen that the amino acids are symmetrically distributed about the tyrosine residue. The amino acids may be considered in the following pairs, tyrosine and glycine amide having no formal partners:

| Pair | General Features |
|------|------------------|
| Ser, Gly | Small side chain, hydrophilic but neutral |
| Trp, Leu | Hydrophobic and neutral |
| His, Arg | Hydrophilic and basic |
| ⌐Glu, Pro | Medium side chain with 5-membered ring, character intermediate but neutral |

In view of the marked structural symmetry, it is not inconceivable that structural symmetry is evident in the active conformation and that the receptor possesses the same symmetry.

Consistent with this concept of symmetry of LH-RH and the receptor therefor, it has now been found that LH-RH analogues of formula (I)

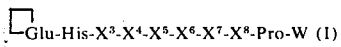
└─Glu-His-X$^3$-X$^4$-X$^5$-X$^6$-X$^7$-X$^8$-Pro-W  (I)

and acid addition salts thereof exhibit LH-RH agonist activity in both in vitro and in vivo tests. As generally accepted and as the term is used herein, an LH-RH agonist is a compound the biological activity of which mimics that of the natural hormone. Thus the compounds of formula (I) and their acid addition salts induce an increase in LH and FSH release when incubated with isolated rat anterior pituitary glands as compared with control results obtained in the absence of such compounds or salts. The compounds of formula (I) and their acid addition salts have also been found to induce ovulation in hamsters whose ovulation has been suppressed by phenobarbital sodium in the manner described by Arimura et al., Science, 174, 511-2 (1971).

In formula (I)

X$^3$ and X$^5$ are the same or different and each is phenylalanyl optionally substituted in the benzene ring;

X$^4$ and X$^6$ are the same or different and each is selected from glycyl, alanyl (D- or L-) and asparaginyl;

X$^7$ is a radical of a neutral hydrophobic non-sulphur containing non-heterocyclic amino acid;

X$^8$ is a radical of a basic amino acid; and

W is selected from glycine amide and a group —NR$^1$R$^2$ where R$^1$, R$^2$ and the nitrogen atom together comprise a group selected from amino, N-alkylamino, N,N-dialkylamino, pyrrolidino, morpholino and 1-methyl-5-aminomethyltetrazolyl, the 'alkyl' having from 1 to 4 carbon atoms and being optionally substituted by an hydroxyl group.

The benzene ring of the radicals X$^3$ and X$^5$ may be substituted with one or more groups selected from alkoxy (e.g. methoxy), halogen (e.g. chlorine), alkyl (e.g. methyl), hydroxyl, nitro and amino; when only one substituent group is present this is preferably in the 4-position with respect to the remainder of the molecule.

As examples of the radical X$^7$ may be mentioned leucyl, isoleucyl, valyl and optionally substituted (as above described in relation to X$^3$ and X$^5$) phenylalanyl.

As examples of the radical X$^8$ may be mentioned arginyl, lysyl, histidyl and homoarginyl.

Insofar as neither the seryl nor the tryptophyl radicals are included in the structure of the compounds of formula (I), these compounds present significant advantages as regards ease of synthesis when compared both with LH-RH itself and with analogues thereof which include either or both of these radicals. An inherent difficulty with the introduction of the seryl radical is that the hydroxyl group therein must be protected if O-acylation is to be avoided. Thus two extra steps are required in any scheme involving introduction of seryl:

protection and subsequent deprotection of the hydroxyl group, of which the former is typically a particularly laborious procedure. The tryptophyl radical readily oxidises, particularly in acid conditions commonly used in peptide synthesis for removal of protecting groups, to yield coloured by-products that are difficult to remove. As a consequence of this peptides such as LH-RH containing the tryptophyl radical are characteristically unstable, a disadvantage not shared by the compounds of formula (I).

As a sub-class within formula (I) are the compounds and the salts thereof wherein $X^3$ and $X^5$ are the same or different and each is phenylalanyl or tyrosyl;

$X^4$ is glycyl or alanyl (D- or L-);

$X^6$ is glycyl;

$X^7$ is leucyl or phenylalanyl;

$X^8$ is arginyl, lysyl or homo-arginyl; and

W is N-alkylamino where the alkyl has 1 or 2 carbon atoms, or 1-methyl-5-aminomethyltetrazolyl.

As a further sub-class may be mentioned the compounds and the salts thereof of the formula $\overset{\ulcorner}{\underset{}{\text{Glu}}}$-His-Phe-$X^4$-Tyr-$X^6$-$X^7$-Arg-Pro-NH.Alk wherein $X^4$ is alanyl or glycyl;

$X^6$ is D-alanyl or glycyl;

$X^7$ is leucyl or phenylalanyl; and

Alk is methyl or ethyl.

It has also been found that the further LH-RH analogues of formula (Ia) and their acid addition salts $\overset{\ulcorner}{\underset{}{\text{Glu}}}$-His-$X^3$-$X^4$-$X^5$-$X^6$-$X^7$-$X^8$-Pro-W (Ia)

wherein $X^3$, $X^4$, $X^5$, $X^6$, $X^7$ and W have the same meanings as in formula (I) and $X^8$ is glycyl or optionally substituted (as above described in relation to $X^3$ and $X^5$) phenylalanyl also exhibit LH-RH agonist activity as above described in respect of the compounds of formula (I), and it will be appreciated that these analogues also possess the synthetic advantages detailed above for these compounds.

The activity of the compounds of formulae (I) and (Ia) resides in the peptide and the acid in the acid addition salts is of less importance although for therapeutic purposes it is preferably pharmacologically and pharmaceutically acceptable to the recipient. Examples of such suitable acids include (a) mineral acids: hydrochloric, hydrobromic, phosphoric, metaphosphoric, nitric and sulphuric acids; (b) organic acids: tartaric, acetic, citric, malic, lactic, fumaric, benzoic, glycollic, gluconic, gulonic, succinic and arylsulphonic, for example p-toluenesulphonic acids.

The pharmaceutically and pharmacologically acceptable acid addition salts together with those salts which are not so acceptable (for example salts of hydrofluoric and perchloric acids) have utility in isolation and purification of the peptides, and of course the unacceptable salts are also valuable in the preparation of the acceptable salts by techniques well known in the art. Those peptides containing a plurality of free amino groups may be obtained in the form of mono- or poly- acid addition salts, or as mixed salts of a plurality of acids.

The compounds of formulae (I) and (Ia) may be prepared by any of the methods known in the art for the preparation of compounds of analogous structure. Thus they may be formed by the sequential coupling of appropriate amino acids using either classical methods of peptide synthesis or solid phase procedures, or by the initial preparation and subsequent coupling of peptide subunits. Such reactions may be effected by, for example, activating the carboxylic acid group of the ingoing amino acid and protecting the non-reacting amino and carboxylic acid groups. Such techniques are standard in the peptide art. Details of suitable activating and protecting (masking) groups and of suitable reaction conditions (both for the coupling reactions and for the removal of protecting groups) giving the minimum of racemisation may be found in the following literature which is given purely by way of exemplification and which is intended to be neither exhaustive nor limiting.

a. Published United Kingdom patent specifications Nos. 1 042 487; 1 048 086; and 1 281 383.

b. Schroder and Luebke, "The Peptides" (Academic Press) (1965).

c. Bellean and Malek, J. Am. Chem. Soc., 90, 165 (1968).

d. Tilak, Tetrahedron Letters, 849 (1970).

e. Beyerman, Helv. Chim. Acta., 56, 1729 (1973).

f. Stewart and Young, "Solid Phase Peptide Synthesis" (W. H. Freeman and Co.) (1969).

It will be appreciated by those skilled in the peptide art that the pyroglutamyl, arginyl and homoarginyl (Har) radicals may not only be incorporated into the compounds of formulae (I) and (Ia) in the fashion described above but may also be formed in situ in the assembled polypeptide chain, or in a peptide subunit thereof, by conversion of a suitable precursor therefor. Thus the arginyl and homoarginyl radicals may readily be formed by guanidation of an ornithyl or lysyl radical respectively, using a reagent such as 1-guanyl-3,5-dimethylpyrazole. The pyroglutamyl radical may be formed by cyclisation of a glutamyl or glutaminyl radical which may itself be introduced in a suitably protected form into the polypeptide or a subunit thereof and deprotected prior to the cyclisation step, as described in for example J. Med. Chem., 14 (1971) 469; Helv. Chim. Acta., 53 (1970) 63; Biochem. Biophys, Res. Comm., 45 (1971) 767,822; and Chem. Berichte, 105 (1972) 2872.

Depending upon the reaction conditions, the compounds of formulae (I) and (Ia) are obtained in the form of the free bases (peptides) or the acid addition salts thereof. The acid addition salts may be converted into the free bases or salts of other acids, and the bases may be converted into acid addition salts thereof, by techniques well known in the art.

It should clearly be understood that the Examples here provided of the preparation of the compounds of formulae (I) and (Ia) are by way of illustration only and are in no way limiting of the synthetic methods and conditions that may be employed.

The compounds of formulae (I) and (Ia) form complexes with pharmaceutically acceptable metals such as zinc, and such complexes exhibit a prolonged period of action in vivo upon parenteral administration as compared with the uncomplexed peptides and their acid addition salts. Such complexes may be prepared by techniques analogous to those well known in the art and as taught in, for example, published South African patent specification No. 73/2419. Thus the zinc complexes may be prepared by, for example, dissolving the peptide in an aqueous solution containing excess zinc ions and optionally also phosphate ions and adjusting the pH with dilute alkali metal hydroxide solution, the complex being then precipitated. The zinc ions may be derived from an ionizable zinc compound such as the chloride or sulphate and the phosphate ions, when present, may be derived from an alkali metal phosphate such as disodium hydrogen phosphate.

The peptides of the formula

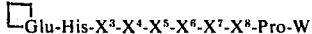-Glu-His-X³-X⁴-X⁵-X⁶-X⁷-X⁸-Pro-W wherein $X^3$, $X^4$, $X^5$, $X^6$, $X^7$, $X^8$ and W have the meanings as above defined in formulae (I) and (Ia), their acid addition salts and their complexes with pharmaceutically acceptable metals may thus be prepared by condensing a reagent (II)

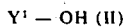  $Y^1 - OH$  (II)

wherein $Y^1$ is selected from pyroglutamyl, a group cyclisable to pyroglutamyl and a partial radical sequence having pyroglutamyl or a group cyclisable thereto at its N-terminal end and from thereon corresponding to the product peptide above defined, with a reagent (III)

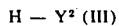  $H - Y^2$  (III)

wherein $Y^2$ corresponds to the balance of the above defined product peptide;

the reagents $Y^1$—OH and H—$Y^2$ being optionally protected and/or activated where and as appropriate and wherein in the groups $Y^1$ and $Y^2$ thereof, as appropriate, any arginyl or homoarginyl radical present in the above defined product peptide is optionally replaced by respectively an ornithyl or lysyl radical, followed if necessary and as appropriate by one or more of the steps of deprotection of the product, cyclisation of the N-terminal group thereof to the pyroglutamyl radical, guanidation of any ornithyl or lysyl radical therein to the arginyl or homoarginyl radical respectively, conversion of the product into the peptide or an acid addition salt thereof, and complexing of the peptide with a pharmaceutically acceptable metal.

In the selection of peptide subunits for synthesis prior to a final condensation step it is common practice to have regard to the following factors. (i) To minimise racemisation, fragments having C-terminal glycyl are advantageous. (ii) Fragments having very low solubility in the solvents normally used in peptide synthesis are disadvantageous. (iii) It is advantageous if the fragments are crystalline.

With regard to the compounds of formulae (I) and (Ia) the reagent $Y^1$—OH identified above preferably corresponds to (a) the N-terminal dipeptide fragment; (b) the N-terminal tetrapeptide fragment; (c) the N-terminal hexapeptide fragment; or (d) the N-terminal heptapeptide fragment of the product peptide, the reagent H-$Y^2$ being chosen appropriately.

Because of their LH-RH agonist activity, as above defined and described, the peptides of formulae (I) and (Ia), their pharmaceutically acceptable acid addition salts and their complexes with pharmaceutically acceptable metals may be used in the treatment of mammals in the fields of both human and veterinary medicine in conditions where the endogenous natural hormone (LH-RH) is absent or where it is desirable that the endogenous levels thereof be supplemented. Thus specific utilities for these peptides, salts and complexes include the following, insofar as the conditions to be treated, where appropriate, have origin in a hypothalamic dysfunction. (i) In the female, the treatment of menstrual cycle disturbances such as amenorrhea; the stimulation of ovulation; and therapy in cases of failure of development of the secondary sexual characteristics. (ii) In males the induction of maturation of spermatozoa and in females the induction of ovulation, for example in therapy in infertility.

A further utility for these peptides, salts and complexes comprises their use, again in both human and veterinary medicine, as diagnostic agents for distinguishing between hypothalamic and anterior pituitary functional disorders or damage.

It will be apparent that quite apart from their value in human medicine these peptides, salts and complexes are of particular commercial value in animal husbandry in promoting fertility in infertile or subfertile animals and thus aiding in the success of the stock breeder.

For each of the utilities mentioned above the amount required of the peptide, salt thereof or complex thereof (hereinafter referred to as the active ingredient) will of course vary both with the particular active ingredient and with the route of administration. In general however for each of these utilities the dosage for nasal or parenteral administration will be in the range 0.005 to 200 μg per kg bodyweight of mammal, preferably 0.01 to 100 μg/kg, and optimally 0.02 to 10 μg/kg; for oral or vaginal administration the dosage will generally be in the range 0.005 to 1000 μg/kg, preferably 0.05 to 200 μg/kg, and optimally 0.2 to 50 μg/kg (all dosages calculated with reference to the base (peptide)).

While it is possible for the active ingredients to be administered as the raw chemical it is preferable, in view of their potency, to present them as a pharmaceutical formulation preparation.

The formulations, both veterinary and for human use, of the present invention comprise an active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof. Desirably the formulations should not include oxidising agents and other substances with which peptides are known to be incompatible.

The formulations include those suitable for oral, rectal, nasal, topical (buccal), vaginal or parenteral (including subcutaneous, intramuscular and intravenous) administration, although the most suitable route in any given case will depend upon the active ingredient. As another possibility an active ingredient may be presented as a depot formulation having slow-release characteristics suiting it for implantation in the body of the recipient, for example sub-cutaneously, intraperitoneally or intravaginally. The formulations may conveniently be presented in unit dosage form and may be prepared by any of the methods well known in the art of pharmacy. All methods include the step of bringing into association with active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; or as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine, the active ingredient in a free-flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent.

Formulations for rectal administration may be presented as a suppository with the usual carriers such as cocoa butter, while a suitable formulation for nasal administration is nasal drops comprising the active ingredient in aqueous or oily solution.

Formulations suitable for topical administration in the mouth include lozenges comprising the active ingredient in a flavoured basis, usually sucrose and acacia or tragacanth; and pastilles comprising the active ingredient in an inert basis such as gelatin and glycerin, or sucrose and acacia.

Formulations suitable for vaginal administration may be presented as pessaries, creams, pastes or spray formulations containing in addition to the active ingredient such carriers as are known in the art to be appropriate.

Formulations suitable for parenteral administration conveniently comprise sterile aqueous solutions of the active ingredient, which solutions are preferably isotonic with the blood of the recipient. Such formulations may be conveniently prepared by dissolving solid active ingredient in water to produce an aqueous solution, and rendering said solution sterile and isotonic with the blood of the recipient.

A suitable slow-release medium for a depot formulation is polyethylene glycol.

It should be understood that in addition to the aforementioned ingredients the formulations of this invention may include one or more additional ingredients such as diluents, buffers, flavouring agents, binders, surface active agents, thickeners, lubricants, preservatives (including anti-oxidants) and the like.

Where the formulation, for human or for veterinary use, is presented in unit dosage form, for example those unit dosage forms specifically mentioned above, each unit thereof conveniently contains the active ingredient (as above defined) in the following amounts, all references being to the base (peptide). For nasal or parenteral administration: 0.25 µg to 10 mg, preferably 0.5 µg to 5 mg, and optimally 1.0 µg to 500.0 µg. For oral or vaginal administration: 0.25 µg to 50 mg, preferably 2.5 µg to 10 mg, and optimally 10 µg to 2.5 mg.

In various aspects therefore the present invention provides:

a. The peptides of formulae (I) and (Ia) as above defined, their acid addition salts and their complexes with pharmaceutically acceptable metals.

b. Methods for the preparation of the peptides, salts and complexes as described above.

c. Pharmaceutical formulations comprising a peptide of formula (I) or (Ia), a pharmaceutically acceptable acid addition salt thereof or a complex thereof with a pharmaceutically acceptable metal, together with an acceptable carrier therefor.

d. Methods for the preparation of the pharmaceutical formulations defined in (c) above.

e. A method for the induction of maturation of spermatozoa (in a male mammal) or for the induction of ovulation (in a female mammal) which comprises the administration to the mammal of a peptide of formula (I) or (Ia), a pharmaceutically acceptable acid addition salt thereof or a complex thereof with a pharmaceutically acceptable metal.

f. A method for the treatment in a mammal of infertility of hypothalamic origin which comprises the administration to the mammal of a peptide of formula (I) or (Ia), a pharmaceutically acceptable acid addition salt thereof or a complex thereof with a pharmaceutically acceptable metal.

The following Examples serve to illustrate the present invention but should not be construed as in any way providing a limitation thereof. All temperatures are in degrees Celsius.

EXAMPLE 1

Preparation of the compound (A)

⌐Glu-His-Phe-Ala-Tyr-Gly-Leu-Arg-Pro-NH.C$_2$H$_5$

This was prepared according to the scheme set out in Table 1, wherein the various protecting and activating groups have the following identities:

Z : benzyloxycarbonyl
Bu$^t$ : t-butyl
CP : 2,4,5-trichlorophenyl
BOC : t-butyloxycarbonyl Active ester couplings were carried out in dimethylformamide at room temperature for 24 hours. Dicyclohexylcarbodiimide couplings were carried out in dimethylformamide; after an initial 30 minutes at −10° C. the reaction mixture was stirred at 4° C. overnight. 1-Hydroxy benzotriazole (1 equivalent) was included in the reaction mixture when two peptides were coupled.

The dipeptide (i) was obtained by the careful saponification of the corresponding methyl ester, followed by extraction with hot dimethyl formamide and subsequent crystallisation from methanol.

The synthesis of pentapeptide (ii) proceeded from H-Leu-OBu$^t$ by the stepwise addition of the appropriate Z-protected amino acid trichlorophenyl esters. At each coupling step, the acylating component was reacted in a slight excess so as to ensure complete conversion. The excess activated ester was then removed by reaction with dimethylaminopropylamine and subsequent extraction with 5% aqueous citric acid.

Table 1

| ⌐Glu | His | Phe | Ala | Tyr | Gly | Leu | Arg | Pro |
|------|-----|-----|-----|-----|-----|-----|-----|-----|
|      |     |     |     |     | Z—OCP | H—OBu$^t$ | | |
|      |     |     |     |     | Z————————OBu$^t$ | | | |

Table 1-continued

| ⌐Glu | His | Phe | Ala | Tyr | Gly | Leu | Arg | Pro |
|---|---|---|---|---|---|---|---|---|
| | | | | Z—OCP | H————————OBu$^t$ | | | |
| | | | | Z———————————————OBu$^t$ | | | | |
| | | | Z—OCP | H————————————OBu$^t$ | | | | |
| | | | Z—————————————————OBu$^t$ | | | | | |
| —OCP | —OCH$_3$ | Z—OCP | H————————————OBu$^t$ | | | | Z—OH | |
| | —OCH$_3$ | Z———————————————OBu$^t$ | | | | | Z—NH . C$_2$H$_5$ | |
| | | | | | | | NO$_2$ | |
| ——(i)——OH | H————————(ii)————————OBu$^t$ | | | | | | BOC⊥OH | H—NH . C$_2$H$_5$ |
| | | | | | | | NO$_2$ | |
| ————————————(iii)————————————OBu$^t$ | | | | | | | BOC⊥——(v)——NH . C$_2$H$_5$ | |
| | | | | | | | NO$_2$ | |
| ————————————(iv)————————————OH | | | | | | | H——⊥——(vi)——NH . C$_2$H$_5$ | |
| | | | | | | | NO$_2$ | |
| ————————————(vii)———————————————————⊥———————————NH . C$_2$H$_5$ | | | | | | | | |
| ————————————(A)———————————————————————————————NH . C$_2$H$_5$ | | | | | | | | |

The removal of trichlorophenol from the Z-peptide-tert-butyl esters was achieved by hydrogenolysis of the Z-group and distribution of the resulting mixture of partially protected peptide and trichlorophenol between ether and 1% acetic acid. Hydrogenolysis was carried out in methanol at atmospheric pressure using a 10% palladium on charcoal catalyst, 0.5g. of catalyst per 10 millimole of peptide. For example, the mixture of Z-Gly-Leu-OBu$^t$ and trichlorophenol was hydrogenated and then treated in the way described. After freeze-drying the aqueous extract and trituration of the resulting solid with ether, H-Cly-Leu-OBu$^t$ was obtained in a crystalline form. The product resulting from coupling Z-Tyr-OCP with H-Gly-Leu-OBu$^t$ was initially obtained as an oil which was purified by treating a methanolic solution of the crude product with DOWEX 2 (a strongly basic anion exchange resin of the polystyrene type).

Dipeptide (i) and the pentapeptide ester (ii) were coupled in the presence of dicyclohexylcarbodiimide and 1-hydroxy benzotriazole. Because of the low solubility of (i) in dimethyl formamide, the reaction was carried out in a mixture of dimethyl formamide and water.

Treatment of the resulting heptapeptide ester (iii) with trifluoroacetic acid in the presence of anisole yielded (iv) which was purified by column chromatography on silica.

The ethylamide of Z-Pro-OH was prepared by a mixed anhydride coupling between Z-Pro-OH and ethylamine. Coupling of BOC(NO$_2$)-Arg-OH with H-Pro-NH.C$_2$H$_5$ resulted in a mixture of the desired protected peptide and the lactam of BOC(NO$_2$)-Arg-OH which was resolved by exhaustive extraction with water of the slightly more hydrophilic dipeptide from an ethyl acetate solution of the mixture. The product (v) obtained by lyophilisation of the aqueous extracts was pure by thin layer chromatography and had the correct elemental analysis.

After deprotection of (v) with hydrochloric acid in acetic acid, the dipeptide (vi) was coupled with (iv) in the presence of dicyclohexylcarbodiimide and 1-hydroxy benzotriazole. The reaction product (vii) was then hydrogenated to yield crude(A), the conditions and catalyst as before except that the solvent was methanol: water: acetic acid, 5:1:1. Purification of the final product (as the diacetate addition salt) was achieved first by column chromatography on silica and then by gradient elution chromatography on carboxymethyl cellulose.

The product was positive to Pauly reagent (for His and Tyr) and Sakaguchi reagent (for Arg); t-butyl hypochlorite/potassium iodide/starch (a general reagent for peptides) revealed only one spot. The product as diacetate addition salt) ran as a single component in thin layer chromatography with each of the following solvent systems:

Chloroform: methanol: 0.880 ammonia, 60 : 45 : 20
Chloroform: methanol: 32% acetic acid, 60 : 45 : 20
n-Butanol: acetic acid: water: ethyl acetate, 1:1:1:1

Amino acid ratios after hydrolysis (6N-hydrochloric acid, 110° C., 24 hours):

Glu : 1.08 His : 1.02 Phe : 1.00 Ala : 1.02 Tyr: 1.00
Gly : 1.03 Leu : 1.03 Arg : 0.96 Pro : 0.99
Recovery: 91% (calculated as the diacetate)

CHARACTERISING DATA a. ⌐Glu-His-OH : m.p. 213°–215° C. : $[\alpha]_D^{28} + 10.5°$ (C = 1, 1% acetic acid)

Analysis: Calculated for $C_{11}H_{14}N_4O_4$ : C, 49.6% : H, 5.27% : N, 21.05% Found: C, 49.47% : H, 5.37% : N, 21.28% b. Compound (A) : $[\alpha]_D^{24} -70.1°$ (C = 1, 1% acetic acid)

Ultra-violet absorption spectrum (in 0.1N sodium hydroxide): $E_{243}$ : 13000 : $E_{293}$ : 2600

Optical rotations were measured on a Bendix-WPL automatic polarimeter.

EXAMPLE 2

By methods analogous to that described in Example 1 there were prepared and purified the following:

└Glu-His-Phe-Gly-Tyr-Gly-Leu-Arg-Pro-NH.C₂H₅ (B)
└Glu-His-Phe-Ala-Tyr-Gly-Leu-Lys-Pro-NH.C₂H₅ (C)
└Glu-His-Phe-Gly-Tyr-Gly-Leu-Lys-Pro-NH.C₂H₅ (D)

In the course of the syntheses the intermediate peptide fragments were initially assembled, in protected forms, and then coupled to give the end product as follows:

B. └Glu-His + (i) Phe-Gly-Tyr-Gly-Leu + (ii) Arg-Pro-NH.C₂H₅

C. └Glu-His + (i) Phe-Ala-Tyr-Gly-Leu + (ii) Lys-Pro-NH.C₂H₅

D. └Glu-His + (i) Phe-Gly-Tyr-Gly-Leu + (ii) Lys-Pro-NH.C₂H₅

In contrast to (v) in Example 1, the dipeptide Z-(BOC)-Lys-Pro-NH.C₂H₅ was obtained without difficulty from Z-(BOC)-Lys-OCP and H-Pro-NH.C₂H₅. Hydrogenolysis, using the conditions of Example 1, and subsequent couplings to the two appropriate heptapeptides yielded analogues (C) and (D).

Each of compounds (B), (C) and (D) (as the diacetate addition salt) ran as a single component in thin layer chromatography with each of the three solvent systems of Example 1. (B) was positive to Sakaguchi reagent and (B), (C) and (D) were positive to Pauly reagent and gave but a single spot with t-butyl hypochlorite/potassium iodide/starch.

Amino acid ratios (after hydrolysis as Example 1):
B. Glu : 1.04 Phe : 0.97 Gly : 2.01 Tyr : 0.97 Leu : 1.00 Pro : 0.95 Recovery : 95% (calculated as the diacetate)
C. Glu : 1.00 His : 0.97 Phe : 0.96 Ala : 0.99 Tyr : 0.96 Gly : 1.04 Leu : 1.00 Lys : 0.98 Pro : 0.93 Recovery : 90% (calculated as the diacetate)
D. Glu : 1.03 His : 1.02 Phe : 0.98 Gly : 2.03 Tyr : 0.98 Leu : 1.00 Lys : 1.02 Pro : 0.88 Recovery : 90% (calculated as the diacetate)

CHARACTERISING DATA a. Optical rotation($[\alpha]_D^{24}$ in 1% acetic acid)
B. −50.2° (C = 1); (C) −63.0° (C = 0.33); (D) −50.8° (C = 1).

b. Ultra-violet absorption spectra (in 0.1N sodium hydroxide) $E_{243}$ : (B) 11500; (C) 10400 ; (D) 11400
$E_{293}$ : (B) 2500 ; (C) 2060 ; (D) 2320

EXAMPLE 3

Preparation of the compounds
└Glu-His-Phe-Ala-Tyr-Gly-Leu-Har-Pro-NH.C₂H₅ (E)
└Glu-His-Phe-Gly-Tyr-Gly-Leu-Har-Pro-NH.C₂H₅ (F)

These were prepared by guanidation of the lysine-8 residues in respectively the compounds identified as (C) and (D) in the foregoing Example 2. Specific details of the preparation of compound (E) are as follows.

1-Guanyl-3,5-dimethyl pyrazole nitrate (24 mg) was dissolved in dimethylformamide (1 ml) and the pH of the solution adjusted to 9-10 with 10% triethylamine in dimethylformamide. A solution of compound (C) (70 mg, 0.059 mM) in dimethylformamide (1 ml) was then added and the mixture stood at room temperature for 4 days. After removal of the solvent the crude product was triturated with ether and purified (as the diacetate addition salt) by concentration gradient elution chromatography on carboxymethyl cellulose.

The purified material (as the diacetate addition salt) chromatographed as a single Pauly and Sakaguchi positive spot in each of the three thin layer chromatography solvent systems of Example 1.

Amino acid ratios (after hydrolysis as Example 1)
Glu: 1.13 His: 0.96 Phe: 0.98 Ala: 1.01 Tyr: 0.96 Gly: 0.99 Leu: 1.00 Har: 0.99 Pro: 0.98

In exactly the same way compound (D) was converted into compound (F). The product (as the diacetate addition salt) was chromatographically homogenous in the three solvent systems previously described and had the following amino acid ratios after acid hydrolysis in the manner of Example 1:
Glu: 1.04 His: 0.98 Phe: 0.99 Gly: 1.95 Tyr: 0.98 Leu: 1.00 Har: 0.97 Pro: 0.96

EXAMPLE 4

Preparation of the compound (G)
└Glu-His-Phe-Gly-Tyr-Gly-Leu-Arg-Pro-1-methyl-5-aminomethyltetrazole┘

The heptapeptide └Glu-His-Phe-Gly-Tyr-Gly-Leu-OH (i) was prepared in a stepwise manner starting from the compound Z-Leu-OBu$^t$ (where Z and Bu$^t$ are as defined in Example 1) and using the 2,4,5-trichlorophenyl esters of benzyloxy carbonyl amino acids in the manner described in Example 1. (See Table 1).

1-Methyl-5-aminomethyl tetrazole hydrochloride was coupled with the p-nitrophenyl ester of benzyloxycarbonyl proline in dimethylformamide in the presence of one equivalent of triethylamine. The reaction mixture was stirred at room temperature overnight and then worked up to yield a crystalline product which melted at 91°–92° C. The benzyloxycarbonyl group was removed by hydrogenolysis, and the resulting N⁵-prolyl-(1-methyl-5-aminomethyl) tetrazole was coupled with

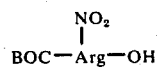

in dimethylformamide (where BOC is as defined in Example 1) using the diimide method. This reaction was accompanied by lactam formation as described in Example 1, and separation of the required product from the contaminating lactam was achieved by a similar method of extraction. Lyophilisation of the aqueous extracts gave a product (ii) which was pure by thin layer chromatography and had the correct elemental analysis.

After deprotection of (ii) in N hydrochloric acid/acetic acid and neutralisation with triethylamine, the dipeptide was coupled with (i) in the presence of dicyclohexylcarbodiimide/hydroxybenzotriazole. The nitro group was removed by hydrogenolysis and the resulting material (as the acetate addition salt) was purified on caboxymethylcellulose.

The product (as the acetate addition salt) was Pauly and Sakaguchi positive and had the following amino acid ratios after acid hydrolysis in the manner of Example 1.
Glu: 0.97 His: 1.03 Phe: 1.00 Gly: 2.09 Tyr: 0.97 Leu: 1.02 Arg: 0.95 Pro: 0.93
Recovery: 83% (calculated as the acetate)

CHARACTERISING DATA

Optical rotation: $\{\alpha\}_D^{24}$ − 46.9° (C = 1; 1% acetic acid).

EXAMPLE 5

Preparation of the compounds
└Glu-His-Phe-Ala-Tyr-Gly-Phe-Arg-Pro-NH.C₂H₅ (H)

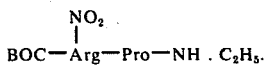Glu-His-Phe-Ala-Tyr-D-Ala-Leu-Arg-Pro-NH.C₂H₅ (K)
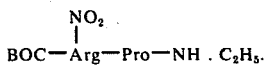Glu-His-Tyr-Ala-Phe-Gly-Leu-Arg-Pro-NH.C₂H₅ (L)
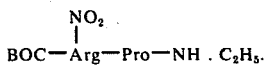Glu-His-Phe-D-Ala-Tyr-Gly-Leu-Arg-Pro-NH.C₂H₅ (M)

In the following BOC represents the t-butyloxycarbonyl group and Bzl represents the benzyl group.

The syntheses of compounds (H) to (M) all proceeded from the common precursor $$\text{BOC—Arg—Pro—NH . C}_2\text{H}_5$$
$$\overset{|}{\text{NO}_2}$$

In each case the next five coupling steps were carried out using the Repetitive Excess Mixed Anhydride (R.E.M.A.) procedure described by Tilak (Tetrahedron Letters, 849 (1970)) and by Beyerman (Helv. Chim. Acta., 56, 1729 (1973)). Each intermediate step was checked for purity by thin layer chromatography. The tyrosine residue in each of these compounds was incorporated as BOC-Tyr(Bzl)-OH, and careful washing was required to remove the excess of this compound from the isolated peptide. The heptapeptides corresponding to the partial sequences 3-9 in compounds (H) to (M) were then each coupled with Glu-His-OH by dicyclohexylcarbodiimide/1-hydroxy benzotriazole mediated reactions. The separation of any unchanged starting materials from the product was readily achieved by gradient elution chromatography after the removal of the remaining protecting groups by hydrogenation.

Specific experimental details for the preparation of compound (H) are as follows.

2.215 g, 5 moles of $$\text{BOC—Arg—Pro—NH . C}_2\text{H}_5$$
$$\overset{|}{\text{NO}_2}$$

were deprotected in 30 ml N-hydrochloric acid/acetic acid for 30 minutes at room temperature. The solvent was removed in vacuo at 35° C and the residue was solidified by trituration with ether. The deprotected peptide was collected by filtration, dried thoroughly over phosphorus pentoxide and sodium hydroxide pellets and then dissolved in 15 ml dimethylformamide. A solution of 505 mg, 5 mmoles of N-methylmorpholine in 2.5 ml dimethylformamide was added and the mixture cooled to −15° C. The mixed anhydride of BOC-Phe-OH was prepared by dissolving 1.99 g, 7.5 mmoles BOC-Phe-OH in 10 ml tetrahydrofuran and adding a solution of 755 mg, 7.5 mmoles N-methylmorpholine in 2.5 ml tetrahydrofuran. This mixture was cooled to −15° C with stirring and a solution of 953 mg, 7.0 mmoles isobutylchloroformate in 2.5 ml tetrahydrofuran was added. After 2 minutes at −15° C the dimethylformamide solution of the amino component was added and the mixture was stirred at −15° C for 2½ hrs. The temperature was then raised to 0° C and the excess mixed anhydride was decomposed by the addition of 7.5 ml 2M-potassium bicarbonate solution. After 30 minutes stirring at 0° C, the mixture was poured onto 200 ml 50% saturated sodium chloride solution and the oily product was extracted into 2 × 150 ml ethyl acetate. The combined ethylacetate extracts were washed with 40 ml of 50% sodium chloride solution and then with 40 ml water. After drying over magnesium sulphate and evaporation of the solvent, the product was solidified by trituration with ether to give $$\text{BOC—Phe—Arg—}$$
$$\overset{|}{\text{NO}_2}$$

The purity of this material was checked by thin layer chromatography in the three solvent systems detailed in Example 1.

By an alternating sequence of deprotections and excess mixed anhydride couplings, carried out in exactly the manner described above, the following intermediate peptides were prepared in chromatographically pure form:

BOC-Gly-Phe-Arg(NO₂)-Pro-NH.C₂H₅
BOC-Tyr(Bzl)-Gly-Phe-Arg(NO₂)-Pro-NH.C₂H₅
BOC-Ala-Tyr(Bzl)-Gly-Phe-Arg(NO₂)-Pro-NH.C₂H₅

The only variation in technique was in the method of work up after decomposition of the excess mixed anhydride. In the cases of the hexa- and heptapeptides, the reaction mixture was poured onto water and the solid product filtered off, washed and dried. The deprotected heptapeptide:

H-Phe-Ala-Tyr(Bzl)-Gly-Phe-Arg(NO₂)-Pro-NH.C₂H₅ (as the hydrochloride addition salt) (1.054 g, 1 mmole) was dissolved in 10 ml dimethylformamide and neutralised with 101 mg N-methylmorpholine in 1 ml dimethylformamide. 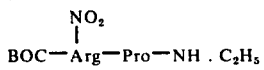Glu-His-OH (319 mg, 1.2 mmole) in 4 ml water was added together with 1-hydroxybenzotriazole (162 mg, 1.2 mmole) in 2,5 ml dimethylformamide. A further 6 ml dimethylformamide was added and the mixture was cooled to −15° C before the addition of 247 mg, 1.2 mmole dicyclohexylcarbodiimide. The reaction mixture was stirred at −15° C for 2 hrs and then at 4° C for 48 hrs. 0.1 ml Acetic acid was added and the temperature was raised to 20° C for 30 minutes before filtering off the dicyclohexylurea. The filtrate was concentrated in vacuo and the residue triturated successively with ether, 5% sodium carbonate solution and water.

The side-chain protecting groups were removed by hydrogenation for 24 hrs. in methanol (30 ml), acetic acid (6 ml) and water (3 ml) in the presence of 0.5 g 10% palladium on charcoal catalyst. The crude deprotected peptide was dissolved in 50 ml 2% acetic acid, filtered to remove some dicyclohexylurea and diluted to 100 ml with water before lyophilisation. The product was then purified of a column of carboxymethylcellulose, eluting with gradients of ammonium acetate, pH 5.1. The peptide (compound (H)) was isolated by pooling the appropriate fractions and repeated lyophilisation to remove ammonium acetate. It proved to be pure on thin layer chromatography with each of the three solvent systems detailed in Example 1.

Compounds (K), (L) and (M) were prepared from BOC-Arg(NO₂)-Pro-NH.C₂H₅ using the R.E.M.A. method as far as the heptapeptide stage, and then by dicyclohexylcarbodiimide/1-hydroxybenzotriazole coupling with the dipeptide 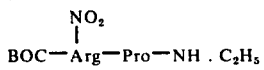Glu-His-OH, precisely in the manner detailed above for compound (H). Each of compounds (K), (L) and (M) appeared pure on thin layer chromatography with the three solvent systems detailed in Example 1.

Amino acid ratios (after acid hydrolysis in the manner of Example 1).

Compound (H) Glu: 1.03 His: 0.97 Phe: 2.00 Ala: 0.95
Tyr: 1.04 Gly: 0.97 Arg: 0.94 Pro: 0.96
Recovery: 85% (calculated as the diacetate).
Compound (K) Glu: 1.02 His: 0.95 Phe: 0.95 Ala: 2.00
Tyr: 0.91 Leu: 1.00 Arg: 0.90 Pro: 0.96
Recovery: 103% (calculated as the diacetate).
Compound (L) Glu: 1.05 His: 1.03 Tyr: 0.99 Ala: 1.02
Phe: 1.00 Gly: 1.07 Leu: 1.00 Arg: 0.94 Pro: 1.02
Recovery 95% (calculated as the diacetate)
Compound (M) Glu: 1.02 His: 0.99 Phe: 0.96 Ala: 0.98
Tyr: 0.95 Gly: 0.98 Leu: 1.00 Arg: 0.93 Pro: 0.99
Recovery: 100% (calculated as the diacetate).
Optical rotations (c=1, 1% acetic acid)

| | |
|---|---|
| (H): $\{\alpha\}_D^{24}$ - 44.5° | (K): $\{\alpha\}_D^{28}$ - 51.8° |
| (L): $\{\alpha\}_D^{26}$ - 60.7° | (M): $\{\alpha\}_D^{27}$ - 36.5° |

EXAMPLE 6

Pharmaceutical Formulations

Two series of each of the formulations detailed below were prepared. In the first series the compound of formula (I) was compound (A) (Example 1) and in the second series the compound of formula (I) was compound (K) (Example 5). In each formulation the appropriate compound was present as the diacetate addition salt but the quantities thereof as given below are calculated with respect to the base (peptide).

i. Tablets (composition per tablet)

| | | | |
|---|---|---|---|
| Compound of formula (I) | 1.0 mg | 5.0 mg | 25.0 mg |
| Starch | 20.0 mg | 20.0 mg | 20.0 mg |
| Lactose | 50.0 mg | 50.0 mg | 50.0 mg |
| Polyvinylpyrrolidone | 8.0 mg | 8.0 mg | 8.0 mg |
| Magnesium stearate | 2.0 mg | 2.0 mg | 2.0 mg |

The compound of formula (I) was intimately mixed with the starch and the lactose, and the mixture granulated using a solution of the polyvinylpyrrolidone in water. The granules were then dried, the magnesium stearate added, and tablets prepared by compression.

ii. Pessaries (composition per passary)

| | | | |
|---|---|---|---|
| Compound of formula (I) | 0.5 mg | 2.5 mg | 12.5 mg |
| Theobroma oil | 1.0 g | 1.0 g | 1.0 g |

The compound of formula (I) was mixed into a smooth paste with a little of the melted theobroma oil at a temperature not exceeding 45° C. The paste was then incorporated into the remaining melted oil and the mixture poured into suitable lubricated moulds and allowed to set.

iii. Vaginal tablets (composition per tablet)

| | | | |
|---|---|---|---|
| Compound of formula (I) | 0.5 mg | 2.5 mg | 12.5 mg |
| Lactose | 500.0 mg | 500.0 mg | 500.0 mg |
| Starch | 450.0 mg | 450.0 mg | 450.0 mg |
| Polyethylene glycol 6000 | 100.0 mg | 100.0 mg | 100.0 mg |
| Magnesium stearate | 10.0 mg | 10.0 mg | 10.0 mg |

The compound of formula (I) was intimately mixed with the starch and the lactose and the mixture granulated using a solution of the polyethylene glycol 6000 in water. The granules were dried, the magnesium stearate added, and tablets formed by compression in a suitably shaped tablet die.

iv. Injection solutions

| | | | |
|---|---|---|---|
| Compound of formula (I) | : 0.04 g | 0.2 g | 1.0 g |
| Dilute acetic acid | : sufficient to produce pH 3.0–4.0 | | |
| Chlorocresol | : 0.1 g | 0.1 g | 0.1 g |
| Water for injections | : to 100.0 ml | | |

The compound of formula (I) was dissolved in 9/10 of the final volume of water adjusted to pH 3.0–4.0 with dilute acetic acid. The chlorocresol was then added and dissolved, and the mixture diluted to volume with the remaining water. The solution was sterilised by passage through a membrane filter, 0.22μ pore size, and then distributed aseptically into 10 ml vials. The vials were each closed with a sterile rubber stopper which was secured with an aluminium collar.

The three solutions detailed above contained respectively 0.4 mg, 2 mg, and 10 mg per ml of the compound of formula (I).

EXAMPLE 7

Preparation of the compound (N)

⌐Glu-His-Phe-Ala-Tyr-Gly-Leu-Gly-Pro-NH.C₂H₅

The pentapeptide H-Phe-Ala-Tyr-Gly-Leu-OBu$^t$ (prepared as in Example 1) was coupled with ⌐Glu-His-OH in the presence of dicyclohexylcarbodiimide/1-hydroxybenzotriazole in aqueous dimethylformamide to give ⌐Glu-His-Phe-Ala-Tyr-Gly-Leu-OBu$^t$. This was deprotected in trifluoroacetic acid containing anisole (1 hr. at room temperature) and the product heptapeptide was purified by dry column chromatography on silica gel using the solvent mixture chloroform: methanol: 0.880 ammonia, 60: 45: 20. The purified material was coupled with H-Gly-OBu$^t$ (dicyclohexylcarbodiimide/1-hydroxybenzotriazole in dimethylformamide) and the resulting octapeptide was deprotected in trifluoroacetic acid/anisole, removing the t-butyl ester group. A further coupling with H-Pro-NH.C₂H₅ (Carbodiimide/triazole in dimethyl formamide as before) yielded the crude nonapeptide (N). Purification was effected first by gradient elution chromatography on carboxymethylcellulose and then by dry column chromatography on silica gel using the system chloroform: methanol: 32% acetic acid, 60: 45: 20. Final purification was achieved by passage through a column of Sephadex G.25, eluting with 2% acetic acid. The final product (as the acetate addition salt) was Pauly positive and was pure on thin layer chromatography with each of the three solvent systems detailed in Example 1.

Amino acid ratios after acid hydrolysis as Example 1:
Glu: 1.09 His: 1.00 Phe: 0.98 Ala: 0.99
Tyr: 0.95 Gly: 2.02 Leu: 1.00 Pro: 1.01
Recovery: 85% (calculated as the acetate) $\{\alpha\}_D^{22}$ − 60.54° (C = 1, 1% acetic acid)

EXAMPLE 8

Preparation of the compound (P)

⌐Glu-His-Phe-Gly-Tyr-Gly-Leu-Phe-Pro-NH.C₂H₅

The pentapeptide H-Phe-Gly-Tyr-Gly-Leu-OBu$^t$ (prepared as in Example 2) was coupled with ⌐Glu-His-OH (dicyclohexylcarbodiimide/1-hydroxybenzotriazole in aqueous dimethylformamide) and the product deprotected in trifluoroacetic acid/anisole (1 hr. at room temperature). The product heptapeptide was purified by dry column chromatography on silica gel using the system chloroform: methanol: 32% acetic acid and then coupled with H-Phe-OBu$^t$ (carbodiimide/triazole as before). After deprotection (trifluoroacetic acid/anisole) and coupling with H-Pro-NH.C$_2$H$_5$ (carbodiimide/triazole) the crude nonapeptide (P) was obtained. This was purified by gradient elution chromatography on carboxymethylcellulose.

The purified (P) (as the acetate addition salt) was Pauly positive and ran as a single component on thin layer chromatography with each of the three solvent systems detailed in Example 1.

Amino acid ratios (after acid hydrolysis as Example 1):

Glu: 1.07 His: 1.00 Phe: 2.10 Gly: 2.03
Tyr: 0.99 Leu: 1.00 Pro: 0.87
Recovery 96% (calculated as the acetate) $\{\alpha\}_D^{22} - 44.71°$ (C = 1, 1% acetic acid)

What we claim is:

1. A peptide of the formula ⌐Glu-His-X$^3$-X$^4$-X$^5$-X$^6$-X$^7$-X$^8$-Pro-W an acid addition salt thereof or a complex thereof with a pharmaceutically acceptable metal, wherein X$^3$ and X$^5$ are the same or different and each is phenylalanyl optionally substituted in the benzene ring with a group selected from the group consisting of methoxy, chlorine, methyl, hydroxyl, nitro, and amino;

X$^4$ and X$^6$ are the same or different and each is selected from glycyl, alanyl (D- or L-) and asparaginyl;

X$^7$ is selected from the group consisting of leucyl, isoleucyl, valyl and phenylalanyl, where the phenylalanyl is optionally substituted in the benzene ring with a group selected from the group consisting of methoxy, chlorine, methyl, hydroxyl, nitro and amino;

X$^8$ is selected from the group consisting of arginyl, lysyl, histidyl, homoarginyl, glycyl and phenylalanyl, where the phenylalanyl is optionally substituted in the benzene ring with a group selected from the group consisting of methoxy, chlorine, methyl, hydroxyl, nitro and amino; and W is selected from glycine amide and a group —NR$^1$R$^2$ where R$^1$, R$^2$ and the nitrogen atom together comprise a group selected from amino, N-alkylamino, N,N-dialkylamino, pyrrolidino, morpholino and 1-methyl-5-aminomethyl tetrazolyl, the 'alkyl' having from 1 to 4 carbon atoms and being optionally substituted by an hydroxyl group, where all references are to the L-amino acids and their radicals except in the case of glycine and unless otherwise stated.

2. A peptide of the formula ⌐Glu-His-X$^3$-X$^4$-X$^5$-X$^6$-X$^7$-X$^8$-Pro-W or an acid addition salt thereof, wherein X$^3$ and X$^5$ are the same or different and each is phenylalanyl optionally substituted in the benzene ring with a group selected from the group consisting of methoxy, chlorine, methyl, hydroxyl, nitro and amino;

X$^4$ and X$^6$ are the same or different and each is selected from glycyl, alanyl and asparaginyl;

X$^7$ is selected from the group consisting of leucyl and phenylalanyl, where the phenylalanyl is optionally substituted in the benzene ring with a group selected from the group consisting of methoxy, chlorine, methyl, hydroxyl, nitro and amino;

X$^8$ is selected from the group consisting of arginyl, lysyl, histidyl and homoarginyl; and W is selected from glycine amide and a group —NR$^1$R$^2$ Where R$^1$, and R$^2$ and the nitrogen atom together comprise a group selected from amino, N-alkylamino, N,N-dialkylamino, pyrrolidino, morpholino and 1-methyl-5-aminomethyl tetrazolyl, the 'alkyl' having from 1 to 4 carbon atoms and being optionally substituted by an hydroxyl group, where all references are to the L-amino acids and their radicals except in the case of glycine.

3. A peptide, acid addition salt thereof or complex thereof as claimed in claim 1 wherein X$^8$ is selected from the group consisting of glycyl and phenylalanyl where the phenylalanyl is optionally substituted in the benzene ring with a group selected from the group consisting of methoxy, chlorine, methyl, hydroxyl, nitro and amino.

4. A peptide, acid addition salt thereof or complex thereof as claimed in claim 1 wherein at least one of X$^4$ and X$^6$ is D-alanyl.

5. A peptide, acid addition salt thereof or complex thereof as claimed in claim 1 wherein when X$^3$, X$^5$, X$^7$ or X$^8$ is phenylalanyl substituted in the benzene ring with a group selected from the group defined in claim 1, said group is in the 4-position with respect to the remainder of the molecule.

6. A peptide, acid addition salt thereof or complex thereof as claimed in claim 5 wherein said group in the 4-position is hydroxyl.

7. A peptide, acid addition salt thereof or complex thereof as claimed in claim 1 wherein X$^8$ is selected from arginyl, lysyl, histidyl and homoarginyl.

8. A peptide, acid addition salt thereof or complex thereof as claimed in claim 1 wherein X$^3$ and X$^5$ are the same or different and each is phenylalanyl or tyrosyl.

9. A peptide, acid addition salt thereof or complex thereof as claimed in claim 1 wherein X$^3$ and X$^5$ are the same or different and each is phenylalanyl or tyrosyl; X$^4$ is glycyl or alanyl (D- or L-); X$^6$ is glycyl; X$^7$ is leucyl or phenylalanyl; X$^8$ is arginyl, lysyl or homoarginyl; and W is N-alkylamino where the alkyl has 1 or 2 carbon atoms, or 1-methyl-5-aminomethyltetrazolyl.

10. A peptide, acid addition salt thereof or complex thereof as claimed in claim 1 wherein X$^3$ is phenylalanyl; X$^4$ is selected from alanyl and glycyl; X$^5$ is tyrosyl; X$^6$ is selected from D-alanyl and glycyl; X$^7$ is selected from leucyl and phenylalanyl; X$^8$ is arginyl and W is N-alkylamino where the alkyl has 1 or 2 carbon atoms.

11. ⌐Glu-His-Phe-Ala-Tyr-Gly-Leu-Arg-Pro-ethylamide as defined in claim 1 or an acid addition salt thereof.

12. ⌐Glu-His-Phe-Gly-Tyr-Gly-Leu-Arg-Pro-ethylamide as defined in claim 1 or an acid addition salt thereof.

13. ⌐Glu-His-Phe-Ala-Tyr-Gly-Leu-Lys-Pro-ethylamide as defined in claim 1 or an acid addition salt thereof.

14. ⌐Glu-His-Phe-Gly-Tyr-Gly-Leu-Lys-Pro-ethylamide as defined in claim 1 or an acid addition salt thereof.

15. ⌐Glu-His-Phe-Ala-Tyr-Gly-Leu-Har-Pro-ethylamide as defined in claim 1 or an acid addition salt thereof.

16. L-Glu-His-Phe-Gly-Tyr-Gly-Leu-Har-Pro-ethylamide as defined in claim 1 or an acid addition salt thereof.

17. L-Glu-His-Phe-Gly-Tyr-Gly-Leu-Arg-Pro-1-methyl-5-amino-methyltetrazole as defined in claim 1 or an acid addition salt thereof.

18. L-Glu-His-Phe-Ala-Tyr-Gly-Phe-Arg-Pro-ethylamide as defined in claim 1 or an acid addition salt thereof.

19. L-Glu-His-Phe-Ala-Tyr-D-Ala-Leu-Arg-Pro-ethylamide as defined in claim 1 or an acid addition salt thereof.

20. L-Glu-His-Tyr-Ala-Phe-Gly-Leu-Arg-Pro-ethylamide as defined in claim 1 or an acid addition salt thereof.

21. L-Glu-His-Phe-D-Ala-Tyr-Gly-Leu-Arg-Pro-ethylamide as defined in claim 1 or an acid addition salt thereof.

22. L-Glu-His-Phe-Ala-Tyr-Gly-Leu-Gly-Pro-ethylamide as defined in claim 1 or an acid addition salt thereof.

23. L-Glu-His-Phe-Gly-Tyr-Gly-Leu-Phe-Pro-ethylamide as defined in claim 1 or an acid addition salt thereof.

24. A pharmaceutically acceptable acid addition salt of a peptide claimed in claim 1.

25. An acetic acid addition salt of a peptide claimed in claim 1.

26. The complex with a pharmaceutically acceptable metal of a peptide claimed in claim 1.

27. The complex with zinc of a peptide claimed in claim 1.

* * * * *